US011707267B2

(12) United States Patent
Sweeney (10) Patent No.: US 11,707,267 B2
(45) Date of Patent: Jul. 25, 2023

(54) INDIVIDUAL PACKAGING ARRANGEMENT FOR ORTHOPEDIC TOOLS

(71) Applicant: Spinal Generations, LLC, Mokena, IL (US)

(72) Inventor: Patrick J. Sweeney, Flossmoor, IL (US)

(73) Assignee: Spinal Generations, LLC, Mokena, IL (US)

( * ) Notice: Subject to any disclaimer, the term of this patent is extended or adjusted under 35 U.S.C. 154(b) by 381 days.

(21) Appl. No.: 16/694,085

(22) Filed: Nov. 25, 2019

(65) Prior Publication Data

US 2020/0085417 A1 Mar. 19, 2020

Related U.S. Application Data

(62) Division of application No. 14/615,241, filed on Feb. 5, 2015, now Pat. No. 10,485,528.

(51) Int. Cl.
*A61B 17/02* (2006.01)
*A61B 90/94* (2016.01)
(Continued)

(52) U.S. Cl.
CPC .............. *A61B 17/02* (2013.01); *A61B 17/17* (2013.01); *A61B 17/3494* (2013.01);
(Continued)

(58) Field of Classification Search
CPC ................... A61F 2/0095; A61B 17/17; A61B 17/1717–1725; A61B 17/865; A61B 50/20; A61B 50/30; A61B 17/02
(Continued)

(56) References Cited

U.S. PATENT DOCUMENTS 4,593,699 A 6/1986 Poncy et al.
4,712,681 A * 12/1987 Branemark ........... A61F 2/0095
206/438

(Continued)

FOREIGN PATENT DOCUMENTS

WO WO-00/07510 2/2000
WO WO-2005/053753 6/2005
(Continued)

OTHER PUBLICATIONS

International Search Report and Written Opinion for PCT Application No. PCT/US2016/015731, dated Apr. 8, 2016, 18 pages.

*Primary Examiner* — Eduardo C Robert
*Assistant Examiner* — Michelle C Eckman
(74) *Attorney, Agent, or Firm* — Foley & Lardner LLP (57) ABSTRACT

A protective member for a medical instrument includes a body portion having an inner side wall defining an interior, configured to receive at least a portion of the medical instrument. The body portion also includes a first end and a second end, wherein at least one of the first end and the second end is configured to at least partially close the respective first end and/or second end of the body portion. The at least partially closed first end and/or second end is configured to be opened for use of the medical instrument, such that the medical instrument can pass through both the first and second ends of the body portion during use, while the inner side wall surrounds a portion of the medical instrument. The body portion is configured for use during a medical procedure using the medical instrument, for example, as a tissue protector or a drilling guide.

20 Claims, 5 Drawing Sheets

(51) Int. Cl.
*A61B 90/90* (2016.01)
*A61B 90/98* (2016.01)
*A61B 50/20* (2016.01)
*A61B 50/30* (2016.01)
*A61B 17/86* (2006.01)
*A61B 17/17* (2006.01)
*A61B 17/34* (2006.01)
*A61B 17/00* (2006.01)
*A61B 50/00* (2016.01)
*A61B 90/00* (2016.01)
*A61B 90/96* (2016.01)

(52) U.S. Cl.
CPC ............ *A61B 17/865* (2013.01); *A61B 50/20* (2016.02); *A61B 50/30* (2016.02); *A61B 90/90* (2016.02); *A61B 90/94* (2016.02); *A61B 90/98* (2016.02); *A61B 90/96* (2016.02); *A61B 2017/00889* (2013.01); *A61B 2050/002* (2016.02); *A61B 2050/005* (2016.02); *A61B 2050/006* (2016.02); *A61B 2050/0054* (2016.02); *A61B 2050/0058* (2016.02); *A61B 2050/0065* (2016.02); *A61B 2050/3008* (2016.02); *A61B 2090/037* (2016.02); *A61B 2090/062* (2016.02); *A61B 2090/08021* (2016.02)

(58) Field of Classification Search
USPC .......................................................... 206/438
See application file for complete search history.

(56) References Cited

U.S. PATENT DOCUMENTS

| | | | | |
|---|---|---|---|---|
| 4,856,648 A * | 8/1989 | Krueger | ............... | A61C 8/0087 |
| | | | | 206/63.5 |
| 4,945,904 A | 8/1990 | Bolton et al. | | |
| 5,441,152 A | 8/1995 | Estes | | |
| 5,445,641 A * | 8/1995 | Frigg | .................... | A61B 17/88 |
| | | | | 606/86 R |
| 5,951,561 A * | 9/1999 | Pepper | ............... | A61B 17/1717 |
| | | | | 606/86 R |
| 6,328,746 B1 * | 12/2001 | Gambale | ............ | A61B 17/8625 |
| | | | | 606/104 |
| 6,436,103 B1 | 8/2002 | Suddaby | | |
| 7,575,579 B2 | 8/2009 | Taras et al. | | |
| 7,766,920 B2 * | 8/2010 | Ciccone | ............... | A61B 17/862 |
| | | | | 606/86 R |
| 8,584,853 B2 | 11/2013 | Knight et al. | | |
| 8,662,299 B2 * | 3/2014 | Pratt | ...................... | A61B 50/30 |
| | | | | 206/339 |
| 8,911,448 B2 | 12/2014 | Stein | | |
| 9,101,349 B2 | 8/2015 | Knight et al. | | |
| 2003/0028178 A1 | 2/2003 | Chin | | |
| 2004/0112781 A1 * | 6/2004 | Hofverberg | .......... | A61C 8/0087 |
| | | | | 206/438 |
| 2005/0059864 A1 | 3/2005 | Fromovich et al. | | |
| 2005/0143756 A1 | 6/2005 | Jankowski | | |
| 2005/0261691 A1 | 11/2005 | Hester et al. | | |
| 2008/0132882 A1 | 6/2008 | Demaria et al. | | |
| 2009/0082789 A1 | 3/2009 | Milliman et al. | | |
| 2009/0266890 A1 * | 10/2009 | Bagozzi | .................... | A61L 2/07 |
| | | | | 235/385 |
| 2010/0030218 A1 * | 2/2010 | Prevost | .................. | A61B 17/17 |
| | | | | 606/80 |
| 2010/0331852 A1 | 12/2010 | Neubardt | | |
| 2012/0172885 A1 * | 7/2012 | Drapeau | ................ | A61B 17/86 |
| | | | | 606/104 |
| 2013/0012999 A1 * | 1/2013 | Petit | ....................... | A61B 50/33 |
| | | | | 606/279 |
| 2014/0020333 A1 | 1/2014 | Knight et al. | | |
| 2014/0343553 A1 | 11/2014 | Ford et al. | | |
| 2015/0073487 A1 | 3/2015 | Crawford et al. | | |
| 2016/0193427 A1 | 7/2016 | Limaye et al. | | |
| 2016/0272410 A1 * | 9/2016 | Roesler | .................. | B65D 85/20 |
| 2016/0331483 A1 * | 11/2016 | Richart | ................ | A61B 17/865 |

FOREIGN PATENT DOCUMENTS

| | | |
|---|---|---|
| WO | WO-2010/011985 | 1/2010 |
| WO | WO-2015/017677 | 2/2015 |

* cited by examiner

INDIVIDUAL PACKAGING ARRANGEMENT FOR ORTHOPEDIC TOOLS

CROSS-REFERENCE TO RELATED PATENT APPLICATION

This application is a divisional of U.S. application Ser. No. 14/615,241, filed Feb. 5, 2015, which is incorporated herein by reference in its entirety.

BACKGROUND

To be safe and effective, medical instruments, such as surgical tools, must be provided to an operating room undamaged and sterilized (e.g., free from contamination from foreign substances or organisms). Surgical tools are sterilized prior to use using a variety of different processes, including steam sterilization, chemical sterilization, and radiation sterilization. Surgical tools may be cleaned sterilized after being used. However, to avoid the costs associated with cleaning and sterilizing surgical tools, single-use, disposable surgical tools may be used. Such disposable surgical tools are sterilized by the manufacturer and provided in a kit.

To maintain sterility, the surgical tools may be sealed in sterile packaging for transport and storage. Some surgical tools, such as blades, gouges, or other cutting instruments may have tips or edges that need to be kept sharp. These tips or edges could be damaged during transport or storage. Additionally, such instruments could potentially damage the packaging in which they are stored and transported, compromising the sterility of the instruments. Some tools may, therefore, be packaged with a protector, such as a silicone sheath slipped over a sharp edge or point. The protector serves both to protect the sharp edges or points from damage and to protect the packaging from being damaged by the sharp edges or points.

Kits containing surgical tools may include tools such as drilling guides and tissue protectors that are configured to provide a passage through which other tools are passed. While necessary for many medical procedures, these tools are often separate from the active surgical tools and represent additional bulk for an inclusive kit.

SUMMARY

One embodiment of the invention relates to a protective member for a medical instrument including a body portion comprising an inner side wall, the inner side wall defining an interior configured to receive at least a portion of the medical instrument. The body portion includes a first end and a second end, wherein at least one of the first end and the second end comprises an end wall coupled to the side wall and configured to at least partially close the respective first end and/or second end of the body portion. The at least partially closed first end and/or second end of the body portion is configured to be opened for use of the medical instrument, such that the medical instrument can pass through both the first and second ends of the body portion during use of the medical instrument while the inner side wall surrounds a portion of the medical instrument. The body portion is configured for use during a medical procedure using the medical instrument.

In some embodiments, the partially closed first end and/or second end of the body portion is separable from the body portion to form a second body portion separate from a main body portion. In certain such embodiments, the side wall comprises a frangible section separating the second body portion from the main body portion. In other embodiments, the second body portion is coupled to the main body portion at a joint. The joint may be one of a threaded joint, a sleeve joint, and a snap-fit joint.

In some embodiments, the medical instrument is completely received within the interior of the body portion. An outer side wall of the body portion may include a plurality of measurement markings disposed on an exterior surface. The protective member may include an identification device. The identification device may be one of a bar code and a radio-frequency identification device. A portion of the body portion may be configured for use as a tissue protector or as a drilling guide. In some embodiments, a portion of the body portion is configured to remain with the medical instrument and be implanted into a patient. In some such embodiments, the portion of the body portion includes an antibacterial material.

A second exemplary embodiment of the invention relates to a method for protecting tissue during a medical procedure. Prior to the medical procedure, the method includes obtaining a medical instrument packaged in and at least partially surrounded by a protective member, wherein the protective member comprises at least one partially closed end portion. During the medical procedure, the method includes opening the at least one partially closed end portion to form a tubular member. The method further includes fixing the tubular member proximate tissue at an incision location to provide a passage of the medical instrument through the tissue to an area of interest, and passing an end of the medical instrument through the open tubular member to the area of interest.

In some embodiments, opening the at least one partially closed end portion includes separating the closed end portion from the protective member. In some embodiments, the protective member acts as a drilling guide to guide the medical instrument to a target position. Accordingly, the tubular member may be fixed at a desired orientation such that the medical instrument passes through the tubular member at the desired orientation. In some embodiments, the method includes positioning the medical instrument into a desired final position and leaving the tubular member attached to the medical instrument and implanted in a body.

A third exemplary embodiment relates to a medical procedure kit including a plurality of medical instruments and a protective member containing at least a portion of one of the plurality of medical instruments. The protective member includes a body portion comprising an inner side wall, the inner side wall defining an interior configured to receive at least a portion of the medical instrument. The body portion further includes a first end and a second end, wherein at least one of the first end and the second end comprises an end wall coupled to the side wall and configured to at least partially close the respective first end and/or second end of the body portion. The at least partially closed first end and/or second end of the body portion is configured to be opened for use of the medical instrument, such that the medical instrument can pass through both the first and second ends of the body portion during use of the medical instrument while the inner side wall surrounds a portion of the medical instrument. The body portion is configured for use during a medical procedure using the medical instrument. The body portion of the protective device may be configured for use as a tissue protector. The body portion of the protective device may be configured for use as a drilling guide.

Alternative exemplary embodiments relate to other features and combinations of features as may be generally recited in the claims.

BRIEF DESCRIPTION OF THE DRAWINGS

The disclosure will become more fully understood from the following detailed description, taken in conjunction with the accompanying figures.

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Figure 1:
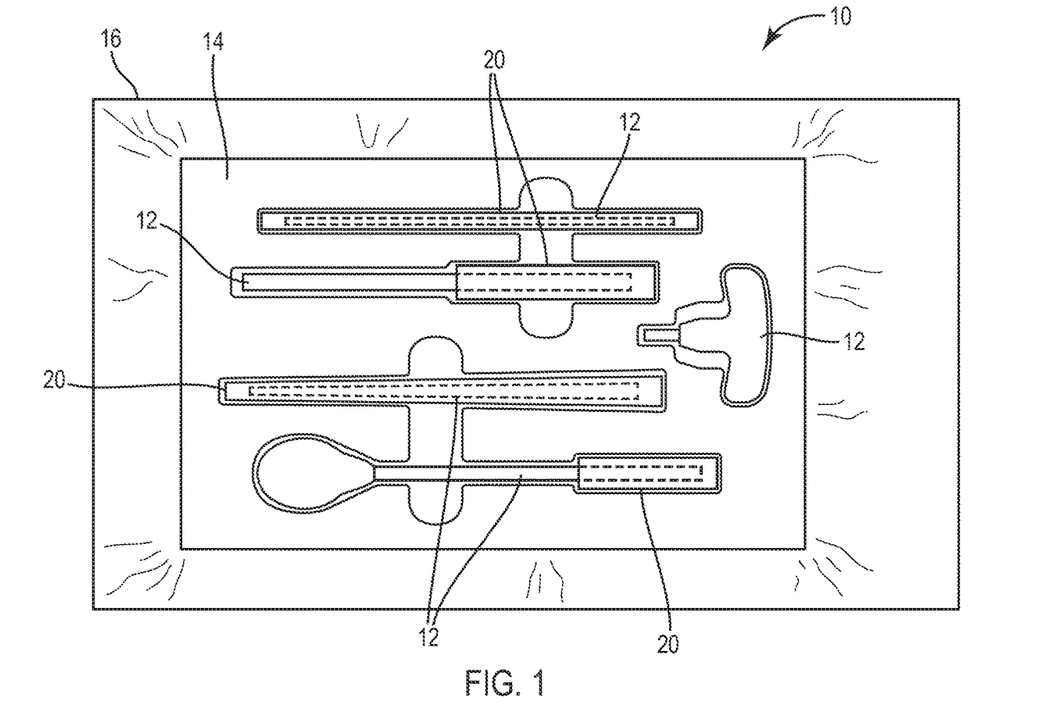
FIG. 1 is a top view of a surgical kit containing a plurality of orthopedic tools packaged in individual protective members, according to an exemplary embodiment.

Referring to FIG. 1, a surgical kit 10 is shown according to an exemplary embodiment. The kit 10 includes one or more tools 12 in a package. The tools 12 may be any suitable surgical or other medical tool that is intended to be sterilized and maintained in a sterilized environment until use, including, but not limited to drills, gouges, saws, nails, screws, guide wires, hooks, blades, clamps, needles, guides, tissue protectors, pins, handles, fixtures, etc. The tools 12 may be formed from any material that is suitable for interacting with biological tissues, such as a metal and metal alloys (e.g., stainless steel, titanium, tungsten carbide, etc.), or a polymer material (e.g., high density polyethylene (HDPE), polycarbonate, polyphenyl-sulfone (PPSF), nylon, etc.), composite materials (e.g., carbon-fiber reinforced polymers, fiberglass reinforced polymers, etc.), or a combination of materials.

The tool 12 may, for example, be a fastener, such as a screw, intended to engage a bone of a patient. The screw may be self-drilling or may be received in a hole that is predrilled with a drill bit. The screw may be fully cannulated, partially cannulated or solid. The kit may include additional tools for use with the screw, such as a guidewire and a drill bit configured to pre-drill a hole in a bone to receive the screw.

A plurality of single use orthopedic tools (e.g., disposable tools) may be provided in a package, such as a sealed pouch, as a part of a kit for a medical procedure. Each of the tools may be at least partially sheathed or contained by a protective member. The protective member protects the orthopedic tool from damage and protect the package from being punctured or otherwise damaged by the orthopedic tools. Additionally, the protective members may serve an additional function as a tissue protector or a drill guide.

According to an exemplary embodiment, the package for the kit 10 includes an inner member, shown as a tray 14, and an outer member, shown as a pouch 16. The tray 14 may be a rigid container that is contoured to receive the individual tools 12. The pouch 16 encapsulates the tools 12 and the tray 14. The tray 14 and/or the pouch 16 may be sealed to maintain the sterility of the tools 12 until the tools 12 are utilized for a surgical procedure.

The tray 14 and the pouch 16 may be formed from materials and by methods that are known in the art for the sterile packaging of medical devices. The tray 14 may be formed from any material that is suitable for maintaining sterility of the tools 12, such as a metal or metal alloy (e.g., stainless steel, etc.), or a polymer material (e.g., HDPE, acrylonitrile butadiene styrene (ABS), etc.). A removable sealing member, such as a film or membrane may be coupled to the tray 14 to provide a microbial barrier to maintain the sterility of the tools 12. The sealing membrane may be formed from a suitable, plastic material. The pouch 16 may be formed from a puncture-resistant material, such as a polymer film (e.g., high density polyethylene), medical grade paper, or a laminate of multiple materials. The pouch 16 may be sealed and configured to resist the penetration of microbes from the outside environment into the interior of the package to maintain the sterility of the tools 12. The kit 10 may be sterilized with any suitable method, including ethylene oxide (EO), gamma, electron-beam, steam (under controlled conditions) and low-temperature oxidative sterilization processes.

Information concerning the tools 12 may be provided on the tray 14 and/or the pouch 16. The information may be provided in the form of a graphic or label applied to the tray 14 and/or the pouch 16. The information may include, for example, the manufacturer, the distributor, the surgical indications, warnings, directions for opening, the tools 12 contained in the kit 10, etc.

By providing the tools 12 in the disposable kit 10, preparation execution of the medical procedure can be simplified by eliminating the need to clean and reprocess instruments prior to every procedure. Disposable, single procedure tools 12 minimize the risk of infection due to cross contamination. For example, the kit 10 may be assembled and sterilized at a manufacturer and then transported to a care facility, where it may be stored prior to use. When needed for surgical procedure, the kit 10 may be opened to provide the sterile tools 10 to the caregiver. The kit 10, as described in more detail below, is configured to be a relatively compact unit, thereby reducing storage and transportation cost and volume.

Figure 2A:
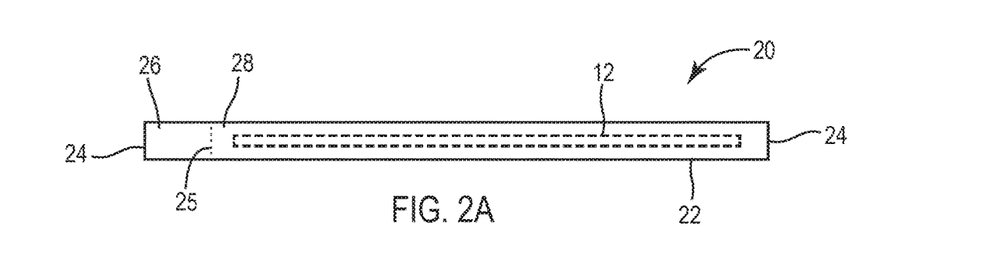
FIG. 2A is a top view of an individual protective member containing an orthopedic tool, according to an exemplary embodiment.
Figure 2B:
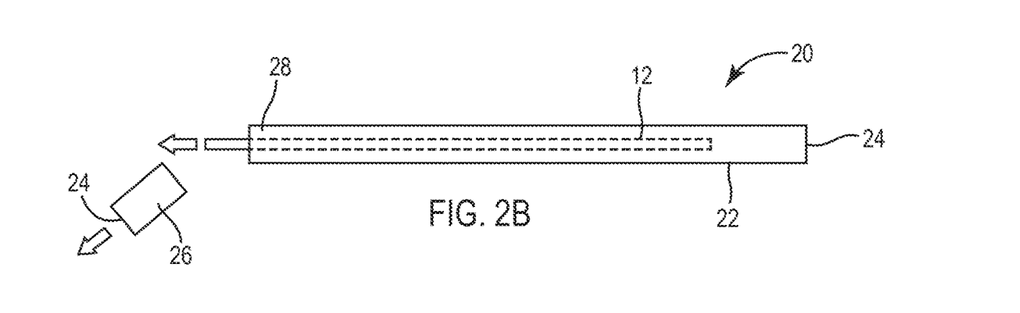
FIG. 2B is a top view of the protective member of FIG. 2A, opened to allow the orthopedic tool to be accessed.

Referring now to FIGS. 2A-2B, at least one of the tools 12 may be individually packaged in a protective member, shown as a tube 20 (e.g., sleeve, container, sheath, cover, etc.). The tube 20 includes a side wall 22 that surrounds at least a portion of the tool 12 (e.g., a pointed or sharp portion of the tool 12) and an end wall 24 that closes an open end of the tube 20. The tube 20 may be closed at one or both ends and may partially or completely enclose the tool 12. The tube 20 may include a graphic, printed label, or other indicia to indicate the identification and characteristics of the tool 12 contained inside the tube 20. In some embodiments, the tube 20 may be color-coded to indicate the identification and characteristics of the tool 12 contained inside the tube 20.

In one embodiment, the tube 20 may be generally cylindrical with a circular cross-sectional shape. In another embodiment, the tube may have another cross-sectional shape (e.g., ovoid, ellipsoid, hexagonal, octagonal, etc.) that provides an exterior surface free of sharp edges or corners that are likely to damage the tray 14 and/or the pouch 16. The tube 20 may have a generally constant cross-section along its length, as shown in FIGS. 2A and 2B or may have a variable cross-section (e.g., flared or tapered). The tube 20 may have outwardly or inwardly extending features, such as ridges or flanges, to accomplish engagement with any separate items or to hold a tool 12 within the tube.

The tube 20 is a hollow, rigid body that is receives at least a portion the tool 12. While the tools 12 may have sharp and/or pointed portions that could potentially damage the tray 14 and/or the pouch 16, the tube 20 is configured to provide a relatively smooth exterior that is free of sharp edges or points and that is less likely to damage the tray 14 and/or the pouch 16. The interior surface of the tube 20 may include features, (e.g., ribs, ridges, flanges, protrusions, etc.) configured to stabilize or otherwise contact the tool 12.

The tube 20 may be formed from any material that substantially protects the tool 12 from damage, such as during transport or handling, and is resistant to being punctured or cut by the tool 12. Because the tube 20 may be utilized as an assistive instrument in a medical procedure, the tube 20 is preferably formed from a biocompatible material. According to an exemplary embodiment, the tube 20 is formed from a metal or metal alloy (e.g., stainless steel, titanium, etc.), a rigid polymer material (e.g., high density polyethylene (HDPE), polycarbonate, polyphenyl-sulfone (PPSF), nylon, PEEK, etc.), composite materials (e.g., carbon-fiber reinforced polymers, fiberglass reinforced polymers, etc.), or a combination of materials.

The tube 20 may be separable into multiple portions. For example, the tube 20 may be a substantially closed body and may be configured to be opened to allow the tool 12 to be removed from the interior of the tube 20, or slid within to the tube 20. As shown in FIGS. 2A-3B, the tube 20 may include a first portion 26 and a second portion 28 that may be separated from each other. In other embodiments, the tube may have three or more portions (e.g., a central portion and two end portions).

Referring still to FIGS. 2A-2B, according to an exemplary embodiment, the tube 20 may include a frangible section 25 at which a first portion 26 of the tube 20 may be removed from a second portion 28. The first portion 26 and the second portion 28 may be formed as a single unitary body and the frangible section 25 may be a section of the tube 20 at which the side wall 22 is weakened, such as by being scored or perforated. After being separated at the frangible section 25, the tube 20 may be removed from the tool 12. Alternatively, the first portion 26 and/or the second portion 28 of the tube 20 may be utilized as an assistive instrument in the medical procedure, as described below.

Figure 3A:
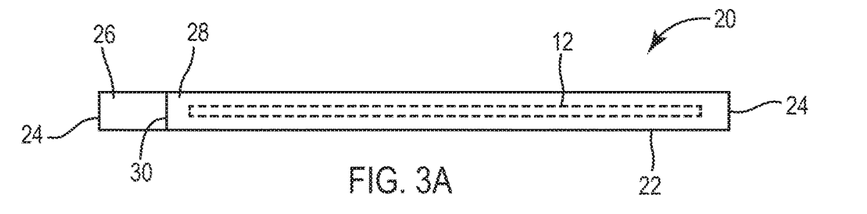
FIG. 3A is a top view of an individual protective member containing an orthopedic tool, according to another exemplary embodiment.
Figure 3B:
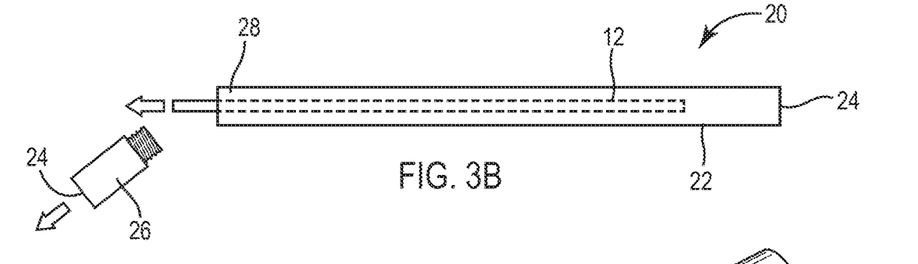
FIG. 3B is a top view of the protective member of FIG. 3A, opened to allow the orthopedic tool to be accessed.

Referring now to FIGS. 3A-3B, in another embodiment, the first portion 26 and the second portion 28 of the tube 20 may be separately formed and may be removably coupled together at a joint 30. According to an exemplary embodiment, the joint 30 is a threaded joint and the first portion 26 is removed from the second portion 28 by rotating the first portion 26 and the second portion 28 relative to each other. In another embodiment, the joint 30 may be another type of joint, such as a sleeve-type joint, or a snap fit joint. After being separated at the joint 30, the tube 20 may be removed from the tool 12. Alternatively, the first portion 26 and/or the second portion 28 of the tube 20 may be utilized as an instrument in the medical procedure, as described below.

Figure 4:
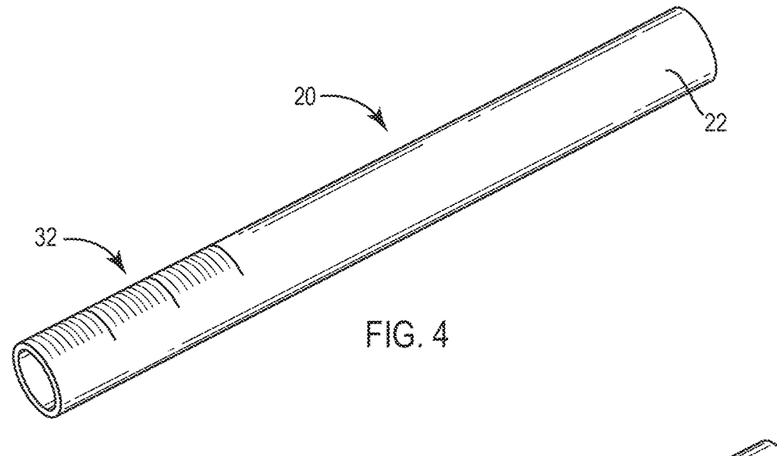
FIG. 4 is a perspective view of the protective member of FIG. 2A, including measurement markings, according to an exemplary embodiment.

Referring now to FIG. 4, the tube 20 may include additional markings 32 or other measurement features. According to an exemplary embodiment, the tube 20 may include markings 32 disposed on the exterior of the side wall 22. The markings 32 may be used to determine depth measurements when used as a tissue protector or guide during the medical procedure and/or to determine lengths of fasteners, such as screws, or other tools housed within the tube 20. Characteristics (e.g., thickness, length, color, etc.) of the markings 32 may vary to facilitate the reading of a measurement from a datum, such as the end of the tube 20 or the tube portion on which the markings 32 are disposed. For example, centimeters and millimeters may be indicated with different styles of markings 32. According to another embodiment, the tube 20 may include one or more slots to indicate distances from a datum.

Figure 5:
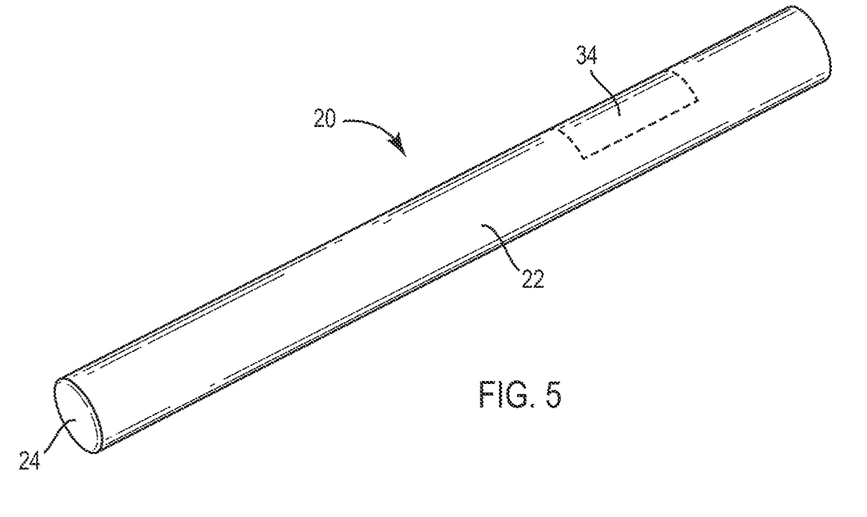
FIG. 5 is a perspective view of the protective member of FIG. 2A, including an identification device, according to an exemplary embodiment.

Referring to FIG. 5, the tube 20 may include an identification feature 34, shown schematically. The identification feature 34 may be utilized to track and identify the tube 20 and the tool 12 contained within the tube 20, such as when shipping the kit 10 from one location to another, for inventory at a location, or to identify the correct tool 12 needed for a particular procedure. The identification feature 34 may be located anywhere on the tube 20. According to one exemplary embodiment, the identification feature 32 may be a bar code or other indicator printed on the outer surface of the tube 20. According to another exemplary embodiment, the identification feature 32 may be an electronic device, such as a radio-frequency identification (RFID) tag coupled to the tube 20. Such an RFID tag may be disposed on the interior surface of the tube 20 or on the exterior surface of the tube 20. Although only a single identification feature 34 is shown in FIG. 5, the tube 20 may include multiple identification features disposed in various locations.

Figure 6:
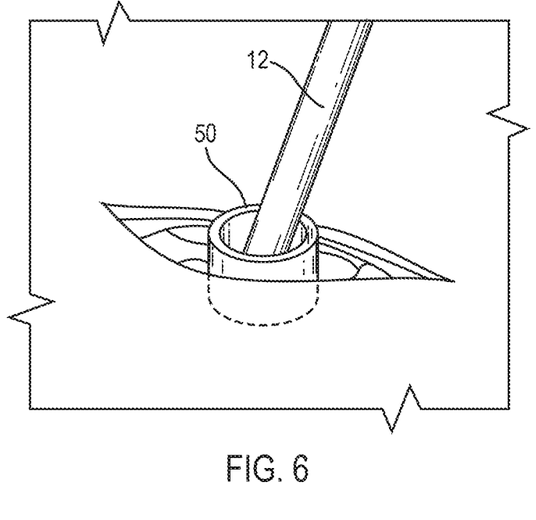
FIG. 6 is a perspective view of the protective member of FIG. 2A utilized as a tissue protector, according to an exemplary embodiment.

Referring now to FIG. 6, in one embodiment, a portion of the tube 20 may be utilized as a tissue protector 50 after the tool 12 has been removed from the tube 20 or the tube 20 manipulated to expose the working end of the tool 12. For example, the end portions of a tube 20 may be removed as described above, with a central portion of the tube 20 being utilized as the tissue protector 50. The tissue protector 50 is a hollow body that is disposed in the area of the medical procedure. The tissue protector 50 provides a passage through which a tool 10 (e.g., a drill bit, screw, gouge, blade, etc.) may pass to an area of interest, such as a portion of bone or other subcutaneous structure. The tissue protector 50 protects surrounding tissue (e.g., skin, subcutaneous structures, etc.) from damage by the tool 12 due to inadvertent contact, such as when inserting, using, or retracting the tool 12. Accordingly, tube 20 utilized as tissue protector 50 is configured to have a similar diameter to the tool 12 being stored therein. For example, the diameter of the tube 20 may have a diameter slightly larger than a screw being positioned in the body. In other embodiments, the diameter may be large enough to accommodate a screw driver that is providing assistance in positioning the screw in the body. The tissue protector 50 may be held in the desired orientation by medical personnel via a handle. The handle may be provided as a part of the kit 10 and may be removably coupled to the tissue protector 50 (e.g., via a threaded connection, via a clamp, etc.). In other embodiments, the handle may be a device such as a hemostat or other medical clamp. In other exemplary embodiments, the tissue protector 50 may be held in the desired orientation directly by the medical personnel or via a stationary brace or fixture that is fixed in relation to the patient.

Figure 7:
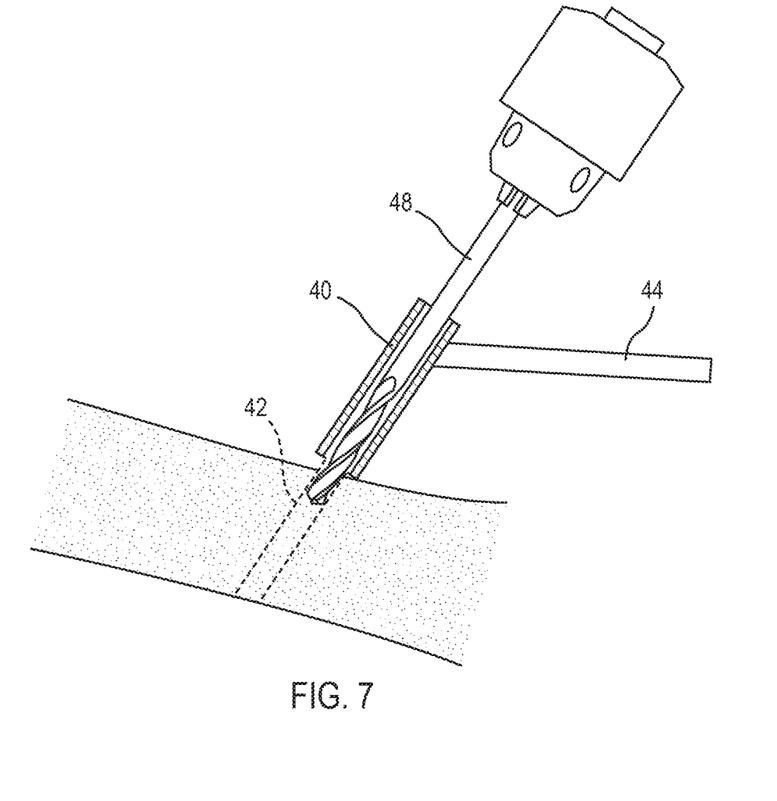
FIG. 7 is a cross-section view of the protective member of FIG. 2A utilized as a drill guide, according to an exemplary embodiment.

Referring now to FIG. 7, in one embodiment, a portion of the tube 20 may be utilized as a drilling guide 40 after the tool 12 has been removed from the tube 20 or the tube 20 moved to expose the working end of the tool 12. For example, the end portions of a tube 20 may be removed as described above, with a central portion of the tube 20 being utilized as the drilling guide 40 for a tool 12 in the form of a drill bit 48. Though FIG. 7 shows tube 20 as a drill guide for a drill bit, it is understood that any other element could also utilize the tube 20 as a guide. For example, a bone screw could be positioned in the body using the tube 20 as a guide. The tube 20 utilized as the drilling guide 40 may in some embodiments be the same tube 20 in which the associated drill bit 48 is stored in the kit 10. The tube 20 may therefore have a similar diameter to the diameter of the drill bit 48 such that there is minimal play between the drill bit 48 and the drilling guide 40. Alternatively, the tube utilized as the drilling guide 40 may be the tube 20 in which the element being positioned, such as the screw, is stored in the kit, and having a diameter large enough for the screw as well as to accommodate passage of a screwdriver shaft therein. Referring back to the drilling guide 40 used for the drill bit 48, the drilling guide 40 may be held at an orientation relative to the patient such that the drill bit 48 passing through the drilling guide 40 forms a hole 42 in the bone of the patient along a desired trajectory thereby allowing for a good engagement of a fastener into the bone, avoiding injury to adjacent soft tissues, and avoiding contact with other hardware (e.g., fasteners, plates, braces, etc.) in the vicinity of the hole 42. According to an exemplary embodiment, the drilling guide 40 may be held in the desired orientation by medical personnel via a handle 44. The handle 44 may be provided as a part of the kit 10 and may be removably coupled to the drilling guide 40 (e.g., via a threaded connection, via a clamp, etc.). In other embodiments, the handle 44 may be a device such as a hemostat or other medical clamp. In other exemplary embodiments, the drilling guide 40 may be held in the desired orientation directly by the medical personnel or via a stationary brace or fixture that is fixed in relation to the patient.

Figure 8:
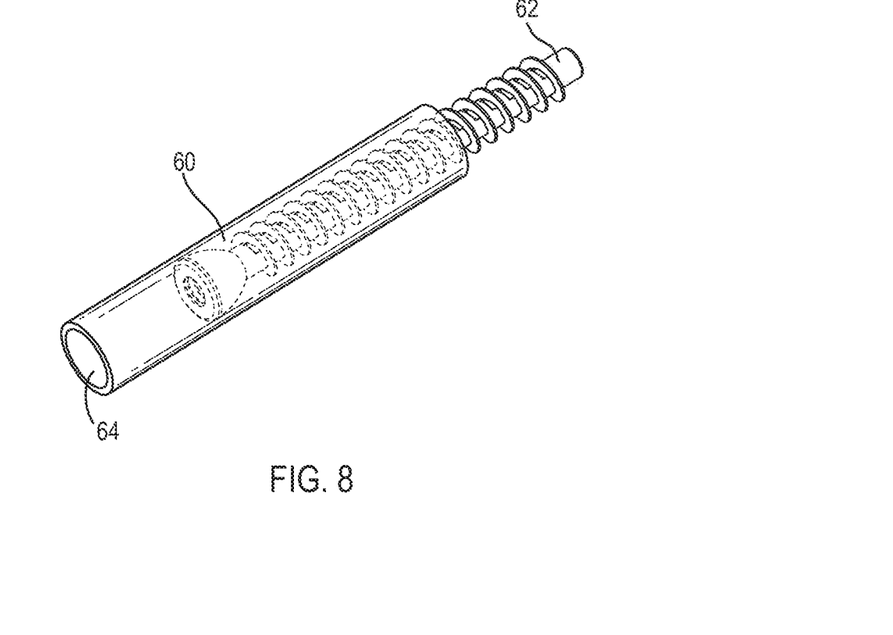
FIG. 8 is a perspective view of a portion of a protective member coupled to a bone screw, according to an exemplary embodiment.

Referring to FIG. 8, in one embodiment, the tube 20 may form a sheath 60 that is coupled to a tool 12 that is in the form of a bone screw 62. The sheath 60 may extend from one end of the screw and provide a body for the medical personnel to grasp during the procedure. A distal end 64 of the sheath 60 may be hollow to allow access to the screw 62, such as to engage the head of the screw 62 with a screwdriver. The opening in the distal end 64 may be large enough to accommodate the shaft of the screwdriver. The sheath 60 may remain coupled to the screw the entire medical procedure or a portion of the medical procedure. For example, the sheath 60 may be disposed in an incision through which the bone is accessed such that it protects the surrounding tissues as the screw 62 is driven into the bone. In some embodiments, all or a portion of the sheath 60 may remain coupled to the screw 62 after the procedure has been completed. Such a sheath 60 may be treated to be antibacterial (e.g., impregnated with antibiotic, silver or other antibacterial materials).

Figure 9A:
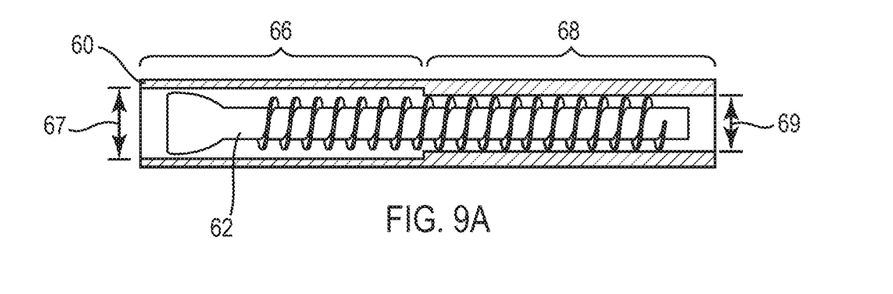
FIG. 9A is a partial cross-section view of a protective member coupled to a bone screw, according to an exemplary embodiment.
Figure 9B:
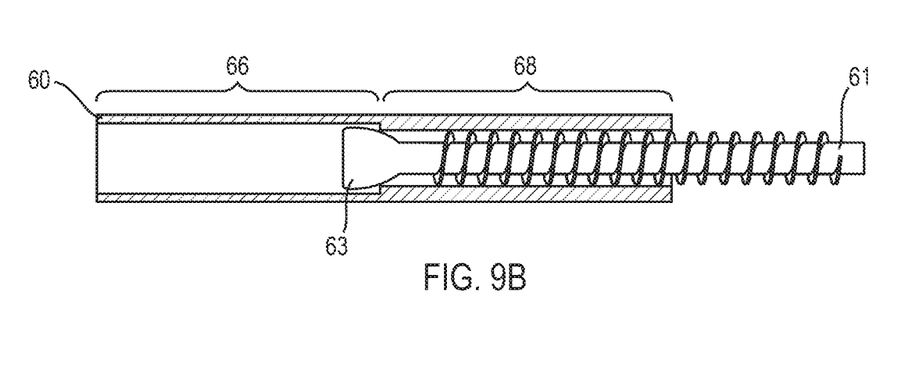
FIG. 9B is a partial cross-section view of the bone screw and protective member of FIG. 9A with the bone screw partially extended out of the protective member.

Referring to FIGS. 9A-9B, the sheath 60 may have a variable internal diameter. For example, the sheath 60 may include a first portion 66 with a first inner diameter 67 and a second portion 68 with a second inner diameter 69. The first diameter 67 is greater than the second diameter 69 and the sheath 60 is configured such that a head portion 63 of the screw 62 can pass through the first portion 66 but is prevented from passing through the second portion 68. In some exemplary uses, the screw 62 and the sheath 60 are inserted into an incision proximate the bone to which the screw 62 will be coupled. The screw 62 is advanced into the bone until the head 63 of the screw 62 is impeded by the second portion 68 of the sheath 60. In this way, the length of a threaded portion 61 of the screw 62 that extends outside of the sheath 60 is limited to a desired length and the sheath 60 acts as a depth control device for the screw 62. Accordingly, the length of the thickened portion having the second inner diameter 69 may be configured with a length according to the desired depth into the bone or the desired distance that the screw, or other device, extends from the sheath.

Figure 10A:
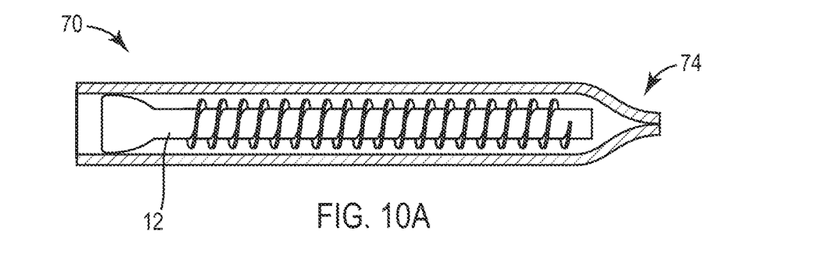
FIG. 10A is a partial cross-section view of a protective member coupled to a bone screw, according to an exemplary embodiment.
Figure 10B:
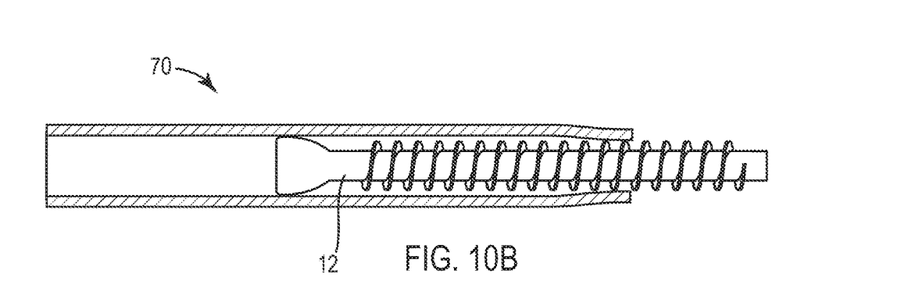
FIG. 10B is a partial cross-section view of the bone screw and protective member of FIG. 10A with the bone screw partially extended out of the protective member.

Referring now to FIGS. 10A-10B, in one embodiment, a tube 20 may form a deformable sheath 70 and the tool, shown as a bone screw 72 contained within the sheath 70 may be utilized to open a closed end 74 of the sheath 70. The closed end 74 of the sheath 70 may be formed, for example, by pinching or otherwise collapsing the sheath 70 such that the inner diameter prevents the screw 72 from advancing out of the sheath 70 through the closed end 74 during transport and handling of the sheath 70 or a kit containing the sheath 70 prior to a medical procedure.

As shown in FIG. 10A, in one embodiment, the closed end 74 may be completely closed. For example, the sheath 70 may be collapsed inward and held together at the closed end with an adhesive, by heat staking, or other appropriate process. In another embodiment, the closed end 74 may not be completely closed and may instead have an inner diameter that is sufficient to retain the screw 72 within the sheath 70. For example, the sheath 70 may be formed with the closed end 74 being formed by a tapered portion of the sheath 70. The pinched or otherwise collapsed shape of the closed end 74 provides a tapered body that facilitates the insertion of the sheath 70 and the screw 72 into an incision. As shown in FIG. 10B, during a medical procedure, the screw 72 may be driven out of the sheath 70 through the closed end 74. The closed end 74 is deformed (e.g., forced open, spread apart, etc.) by the screw 72, allowing the screw 72 to exit the sheath 70, pushing outward on the surrounding tissue and protecting the surrounding tissue from the screw 72.

Figure 11:
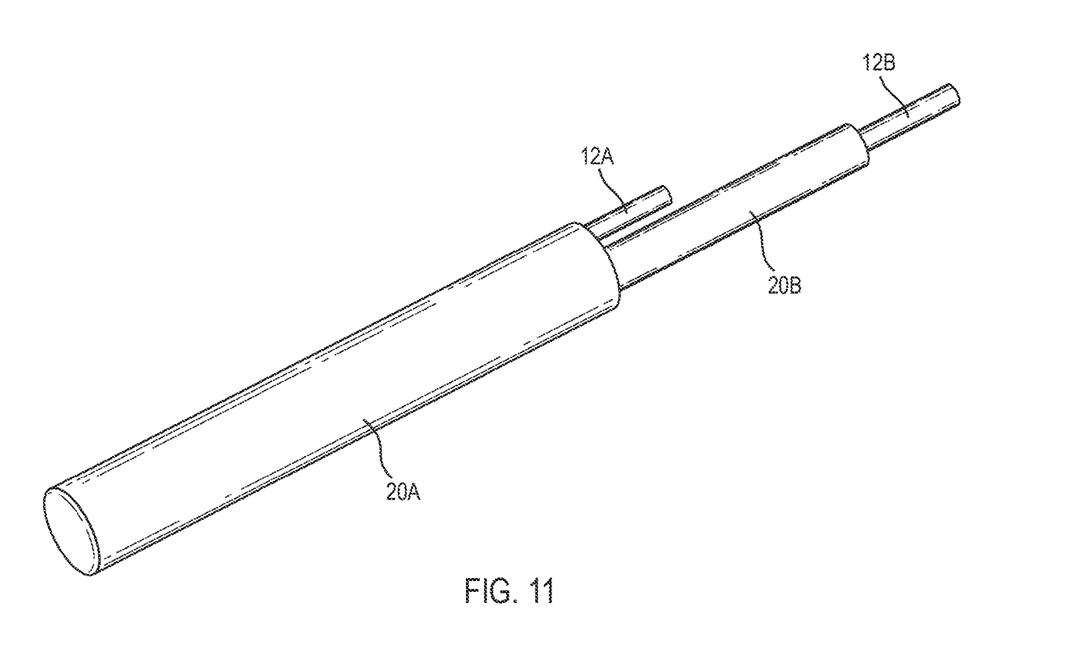
FIG. 11 is a schematic view of a system of nested tools and protective members, according to an exemplary embodiment.

Referring now to FIG. 11, in some embodiments, multiple tubes 20 and tools 12 may be nested to save additional space. A first tube 20A may be large enough in diameter to enclose a second tube 20B, which may, in turn, enclose one or more tools 12B. The first tube 20A may enclose one or more tools 12A in addition to the second tube 20B.

The tubes 20 and tools 12 are described above as being single-use items that are provided as a kit 10 within the tray 14, pouch 16, or other sterilized packaging. In other exemplary embodiments, the tools 12 and the tubes 20 can be packaged and provided individually, and not contained within a kit. In other exemplary embodiments, the tubes 20 and the tools 12 contained within the tubes 20 may be steam sterilized (e.g., using an autoclave) or otherwise sterilized and may be provided separately from any additional packaging. In other embodiments, the tubes 20 and/or the tools 12 may be configured to be sterilized after use and reused.

Further modifications and alternative embodiments of various aspects of the invention will be apparent to those skilled in the art in view of this description. Accordingly, this description is to be construed as illustrative only. The construction and arrangements of the bone screws and inserts, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A protective member configured as part of a packaging, the protective member shaped to contain an orthopedic device, the protective member comprising:
   a body portion defining a central axis and comprising an inner side wall and an outer side wall, the inner side wall defining an interior configured to receive at least a portion of the orthopedic device, wherein the inner side wall and the outer side wall extend coaxially about the central axis and in a direction parallel to the central axis, and wherein the body portion further comprises:
   a first end and a second end, the first end and the second end at least partially open such that the orthopedic device can pass through both the first and second ends of the body portion during use of the orthopedic device while the inner side wall surrounds a portion of the orthopedic device disposed within the interior of the body portion,
   wherein in a first configuration the first end and the second end are closed such that the body portion encloses the orthopedic device within the body portion, and in a second configuration at least one of the first end or the second end at least partially open such that the orthopedic device passes through the body portion; and
   a handle extending outwardly from the outer side wall of the body portion of the protective member, the handle comprising a first end coupled with the outer side wall and a second end opposite the first end.

2. The protective member of claim 1, wherein the body portion comprises a cylindrical geometry arranged concentrically about the central axis.

3. The protective member of claim 1, wherein the body portion comprises at least one of a metal, a metal alloy, or a rigid polymer material.

4. The protective member of claim 1, wherein the handle extends from the outer side wall at an oblique angle relative to the central axis of the body portion.

5. The protective member of claim 1, wherein the handle is removably coupled with the outer side wall of the body portion, wherein the outer side wall of the body portion comprises a first coupler and the first end of the handle comprises a second coupler, the first and second couplers being complimentary.

6. The protective member of claim 5, wherein the first and second couplers comprise a threaded connection.

7. The protective member of claim 1, wherein the orthopedic device is at least one of a drill bit or a bone screw.

8. The protective member of claim 1, wherein the handle is configured to be secured to a stationary fixture such that the protective member maintains a desired orientation.

9. The protective member of claim 1, wherein the first and second ends of the body portion are at least partially closed and configured to be opened by the orthopedic device so as to at least partially receive the orthopedic device within the interior of the protective member.

10. The protective member of claim 1, wherein the body portion is configured accommodate the orthopedic device as well as a tool configured to manipulate the orthopedic device within the interior of the body portion.

11. A medical kit, comprising:
   a package shaped to contain an orthopedic tool in a protective member, the package having an outer layer configured to maintain sterility of the orthopedic tool, the protective member configured to accommodate the orthopedic tool and prevent the orthopedic tool from puncturing the outer layer, the protective member comprising:
   a body portion defining a central axis and comprising an inner side wall and an outer side wall, the inner side wall defining an interior configured to receive at least a portion of the orthopedic tool, wherein the inner side wall and the outer side wall extend coaxially about the central axis and in a direction parallel to the central axis, and wherein the body portion further comprises:
   a first end and a second end, the first end and the second end at least partially open such that the orthopedic tool can pass through both the first and second ends during use of the orthopedic tool while the inner side wall surrounds a portion of the orthopedic tool disposed within the interior of the body portion,
   wherein in a first configuration the first end and the second end are closed such that the body portion encloses the orthopedic device within the body portion, and in a second configuration at least one of the first end or the second end at least partially open such that the orthopedic device passes through the body portion; and
   a handle extending outwardly from the outer side wall of the body portion of the protective member, the handle comprising a first end coupled with the outer side wall and a second end opposite the first end.

12. The protective member of claim 11, wherein the body portion comprises a cylindrical geometry arranged concentrically about the central axis.

13. The protective member of claim 11, wherein the first and second ends are at least partially closed and configured to be opened by the orthopedic tool so as to receive the orthopedic tool at least partially within the interior of the protective member.

14. The protective member of claim 11, wherein the handle extends from the outer side wall at an oblique angle relative to the central axis of the body portion.

15. The protective member of claim 11, wherein the handle is removably coupled with the outer side wall of the body portion, wherein the outer side wall of the body portion comprises a first coupler and the proximal end of the handle comprises a second coupler, the first and second couplers being complimentary.

16. The protective member of claim 15, wherein the first and second couplers comprise a threaded connection.

17. The protective member of claim 11, wherein the orthopedic tool is at least one of a drill bit or a bone screw.

18. The protective member of claim 11, wherein the handle is configured to be secured to a stationary fixture such that the protective member maintains a desired orientation.

19. The protective member of claim 11, wherein the body portion is configured accommodate the orthopedic tool as well as an instrument configured to manipulate the orthopedic tool within the interior of the body portion.

20. A protective member for an orthopedic tool, comprising:
- a body portion defining a central axis and comprising a cylindrical geometry with an inner side wall and an outer side wall, the inner side wall defining an interior configured to receive at least a portion of the orthopedic tool, wherein the inner side wall and the outer side wall extend coaxially about the central axis and in a direction parallel to the central axis, and wherein the body portion further comprises:
  - a first end and a second end, the first end and the second end at least partially open such that the orthopedic tool can pass through both the first and second ends of the body portion during use of the orthopedic tool while the inner side wall surrounds a portion of the orthopedic tool disposed within the interior of the body portion,
  - wherein in a first configuration the first end and the second end are closed such that the body portion encloses the orthopedic device within the body portion, and in a second configuration at least one of the first end or the second end at least partially open such that the orthopedic device passes through the body portion; and
- a handle extending outwardly at an oblique angle from the outer side wall and configured to be held so as to arrange the body portion in a desired orientation and prevent the body portion from deviating from the desired orientation,
- wherein the handle comprises a first end and a second end opposite the first end, the first end comprising a coupler configured to removably couple the handle to the outer wall of the body portion.

* * * * *